United States Patent [19]

Goroff

[11] Patent Number: 5,229,275
[45] Date of Patent: Jul. 20, 1993

[54] IN-VITRO METHOD FOR PRODUCING ANTIGEN-SPECIFIC HUMAN MONOCLONAL ANTIBODIES

[75] Inventor: Diana K. Goroff, Chevy Chase, Md.

[73] Assignee: Akzo N.V., Arnhem, Netherlands

[21] Appl. No.: 514,775

[22] Filed: Apr. 26, 1990

[51] Int. Cl.$^5$ ............... C12P 21/08; C12N 5/06; C07K 15/26

[52] U.S. Cl. ............... 435/70.1; 435/70.21; 435/70.4; 435/240.27; 435/240.2; 530/351; 530/387.1; 530/388.1; 424/85.2

[58] Field of Search ............... 435/70.21, 70.4, 240.27, 435/70.1, 240.2; 530/351, 387, 387.1, 388.1; 424/85.2; 544/265

[56] References Cited

U.S. PATENT DOCUMENTS 4,904,584  2/1990  Shaw .................. 424/85.1

FOREIGN PATENT DOCUMENTS 0341065  5/1989  European Pat. Off. .
8600927  2/1986  World Int. Prop. O. .

OTHER PUBLICATIONS

D. N. Copsey et al., *Genetically Engineered Human Therapeutic Drugs*, 1988, pp. 13 and 109–111.
A. L. Luzzati et al., *Nature* 269: 419–420, 29 Sep. 1977.
S. Gillis, *Fundamental Immunology, Second Edition*, pp. 621–638, 1989.
Goding, *Monoclonal Antibodies: Principles and Practice*, 1983, pp. 37, 71 and 85.
M. G. Goodman, "Immunobiologic Properties of the C8-Derivatized Guanine Ribonucleosides", Biomedicine & Pharmacotheraphy, 37, 344–350 (1983).
M. G. Goodman et al., "Derivatized Guanine Nucleosides: A New Class of Adjuvant for In Vitro Antibody Responses", J. of Immuno., 130, 2580–2585 (1983).
L. Danielsson et al., "Effect of Cytokines on Specific In Vitro Immunization of Human Peripheral B Lymphocytes Against T-cell Dependent Antigens", Immunology, 61, 51–55 (1987).
M. G. Goodman, "Role of Salvage and Phosphorylation in the Immunostimulatory Activity of C8-Substituted Guanine Ribonucleosides", J. Immuno., 141, 2394–2399 (1988).
M. G. Goodman et al., "Enhancement of the Human Antibody Response by C8-Substituted Guanine Ribonucleosides in Synergy with Interleukin 2", J. Immuno., 135, 3284–3288 (1985).
M. G. Goodman, "Interaction Between Cytokines and 8-Mercaptoguanosine in Humoral Immunity: Synergy with Interferon", J. Immuno., 139, 142–146 (1987).
G. T. Rijkers et al., "8-Mercaptoguanosine Overcomes Unresponsiveness of Human Neonatal B Cells to Polysaccharide Antigens", J. of Immunology, 141, 2313–2316 (1988).
W. V. Scheuer, et al., "Enhancement of the In Vivo Antibody Response by an 8-Derivatized Guanine Nucleoside", Cellular Immunology, 91, 294–300 (1985).
M. G. Goodman and W. O. Weigle, "Manifold Amplification of In Vivo Immunity in Normal and Immunodeficient Mice by Ribonucleosides Derivatized at C8 of Guanine", Proc. Natl. Acad. Sci. USA, 80, 3452–3455 (1983).

Primary Examiner—Robert A. Wax
Assistant Examiner—Stephen Walsh
Attorney, Agent, or Firm—Donna Bobrowicz

[57] ABSTRACT

A method of amplifying production of IgG, IgA and IgM antigen specific human monoclonal antibodies from transformed, T-cell depleted, human peripheral blood lymphocytes through the use of an adjuvant system consisting of 8-mercaptoguanosine and at least one of the cytokines interleukin-4 and interleukin-6. Also included in the invention is the adjuvant system and a kit comprising the system.

8 Claims, 5 Drawing Sheets

IN-VITRO METHOD FOR PRODUCING ANTIGEN-SPECIFIC HUMAN MONOCLONAL ANTIBODIES

BACKGROUND OF THE INVENTION

This invention relates to a method of amplifying production of IgG, IgA and IgM antigen-specific human monoclonal antibodies from Epstein Barr virus (EBV) transformed, T-cell depleted human peripheral blood lymphocytes through the use of an adjuvant system consisting of 8-mercaptoguanosine and at least one of the cytokines interleukin-4 (IL-4) and interleukin-6 (IL-6). It also includes the adjuvant system and a kit comprising such system.

Monoclonal antibodies derived from mice are the reagents most commonly used in in vivo therapeutic and diagnostic procedures and for in vitro diagnostic testing. Although a good deal of success has been had with the use of these murine monoclonals, a major disadvantage is that they are not identical to antibodies produced by humans. Because of the species differentiation, when use is made of murine monoclonal antibodies in the in vivo diagnostic or therapeutic treatment of humans, it is now known that anti-murine antibodies may be produced in the treated patient. The presence of these anti-murine antibodies can sensitize the patient to the degree that additional therapy or in vivo diagnostic testing using murine monoclonal antibodies is precluded. In vitro test results on sensitized patients also may be rendered erroneous due to interactions of the anti-murine antibodies with the murine antibodies in the diagnostic assay. In order to eliminate these problems, the monoclonal antibody of choice, especially for use in vivo, is one derived from humans.

Although it is theoretically possible to produce human antibodies using cells from various organs, such as the spleen or the tonsils, the most readily available souce is the peripheral blood supply.

It is known to those skilled in the art that it is possible to produce antigen specific monoclonal antibodies derived from human peripheral blood lymphocytes (PBL). Unfortunately, the success rate for producing antigen specific human antibodies of the right isotype is difficult and particularly time consuming. The majority of research on monoclonal antibody production has been performed on the murine model, and the use of PBL is a newer field. Since the donor generally is not and cannot be immunized prior to donating blood, the B cells from the PBL must be exposed to the proper antigen, and thereby activated, only in vitro. The activation by the antigen begins the cycle that continues with proliferation of the B cells and then differentiation of these cells into antibody producing cells. Once these cells produce antibodies to the antigen, it has generally been found that the IgM isotype is the isotype most commonly produced. However, the isotype of choice for many applications is IgG.

It is well known that presentation of antigen in vitro is very difficult to do technically. Enhancement of antigen specific B cell activation, proliferation and differentiation is known to occur with a class of compounds known as C8-substituted guanine ribonucleosides (M. G. Goodman, "Immunobiologic properties of the C8-Derivatized Guanine Ribonucleosides", Biomedicine & Pharmacotherapy, 37, 344-350 (1983); M. G. Goodman et al., "Derivatized Guanine Nucleosides: A New Class of Adjuvant for In Vitro Antibody Responses", J. of Immuno., 130, 2580-2585 (1983); L. Danielsson et al., "Effect of Cytokines on Specific In Vitro Immunization of Human Peripheral B Lymphocytes Against T-cell Dependent Antigens", Immunology, 61, 51-55 (1987); M. G. Goodman, "Role of Salvage and Phosphorylation in the Immunostimulatory Activity of C8-Substituted Guanine Ribonucleosides", J. Immuno., 141, 2394-2399 (1988); W. J. Hennen et al., EPA 0 341 065, "Immunostimulating Guanine Derivatives, Compositions and Methods".) Some of the more active compounds are 8-bromoguanosine, 8-mercaptoguanosine and 7-methyl-8-oxoguanosine. Although the specific mode of activation is not precisely known, the C8-derivatized guanine ribonucleosides, and in particular, 8-mercaptoguanosine (8-MG), have the capability to enhance B-cell activation to produce an antigen specific antibody producing cell. Thus, while the number of antigen specific B-cells present in PBL at the initiation of culture may be less than 1 in $10^6$–$10^7$ cells, the addition of 8-MG allows preferential clonal expansion of those cells responding to antigen in vitro.

L. Danielsson et al. (see above) have investigated the effect of cytokines in the antigen specific activation of human B lymphocytes. Both T-cell depleted and unseparated PBL were used in conjunction with haemocyanin as the antigen and mouse recombinant IL-1 and human recombinant IL-2, along with other cytokines as the adjuvants, in this study. It was discovered that no in vitro immunization occurred in unseparated PBL. In T-cell depleted PBL, antigen specific human B cells were found and differentiation was improved with the addition of B cell differentiation factor and IL-2. Addition of IL-1 had only a negligible effect. However, the use of a B cell differentiation factor, in this case, pokeweed mitogen T-cell replacing factor, was absolutely necessary to obtain any response at all.

In 1985, Goodman and Weigle studied the antigen specific primary antibody response of T-cell depleted PBL in vitro, using 7-methyl-8-oxoguanosine and IL-2. The results show that this combination of adjuvants in a T-cell depleted PBL system generated an antigen specific antibody response. 7-methyl-8-oxoguanosine was tested as the only adjuvant, as was 8-MG. While 7-methyl-8-oxoguanosine consistently induced a high degree of enhancement of the antibody response, 8-MG induced a much smaller response. (M. G. Goodman et al., "Enhancement of the Human Antibody Response by C8-Substituted Guanine Ribonucleosides in Synergy with Interleukin 2", J. Immuno., 135, 3284-3288 (1985)).

Later, a similar study was done in order to determine if various cytokines were able to synergise with 8-MG to augment B cell responsiveness to antigen. Murine cell lines were used. The data indicated that synergistic effects did not occur with interferon-gamma, purified IL-1, IL-2, IL-3, IL-4 or IL-5, but did with interferon-alpha and interferon-beta. (M. G. Goodman, "Interaction Between Cytokines and 8-Mercaptoguanosine in Humoral Immunity: Synergy with Interferon", J. Immuno., 139,142-146 (1987)).

Another problem facing investigators attempting to raise human monoclonals from PBL is the need for IgG and IgA isotypes. Efforts to immortalize antigen specific antibody producing B cells use traditional protocols, such as transformation of these cells with EBV. Unfortunately, EBV transformed cells produce antibodies preferentially of the IgM isotype. A method for producing human polyclonal antibodies containing substantially less IgM and substantially more IgG and IgA than is currently known is needed. These human monoclonal antibody producing cells could then be harvested, cloned and used to produce human monoclonal antibodies in cell culture.

SUMMARY OF THE INVENTION

The present invention is a method of amplifying production of antigen specific human monoclonal antibodies in vitro, primarily of the IgG and IgA isotypes, but also of antigen specific IgM, using T-cell depleted human, EBV transformed peripheral blood lymphocytes cultured with 8-mercaptoguanosine (8-MG) and IL-4, 8-MG and IL-6, or 8-MG and IL-4 and IL-6. In particular, the invention is a method comprising:

a) obtaining human peripheral blood lymphocytes (PBL), b) depleting T-cells from said PBL using standard methods, c) transforming the T-cell depleted PBL with Epstein Barr virus in the presence of antigen and an adjuvant selected from the group 8-MG and IL-4; 8-MG and IL-6; or 8-MG, IL-4 and IL-6;

d) identifying cells producing antigen specific IgG and IgA antibodies, and e) cloning said identified cells to produce cell lines to be used for the manufacture of antigen specific IgG, IgA and IgM monoclonal antibodies.

The addition of 8-MG and antigen to cultured T-cell depleted EBV transformed PBL dramatically increases the chances of transforming B cells that produce antibodies of interest by expanding the antigen-specific clones early in the course of the culture period. The addition of IL-4 and IL-6 to the culture enhances B cell differentiation and isotype switching resulting in a 20–40 fold increase in the production of polyclonal antibodies (PCA) compared to PBLs infected with EBV alone.

DETAILED DESCRIPTION OF THE INVENTION

Figure 1:
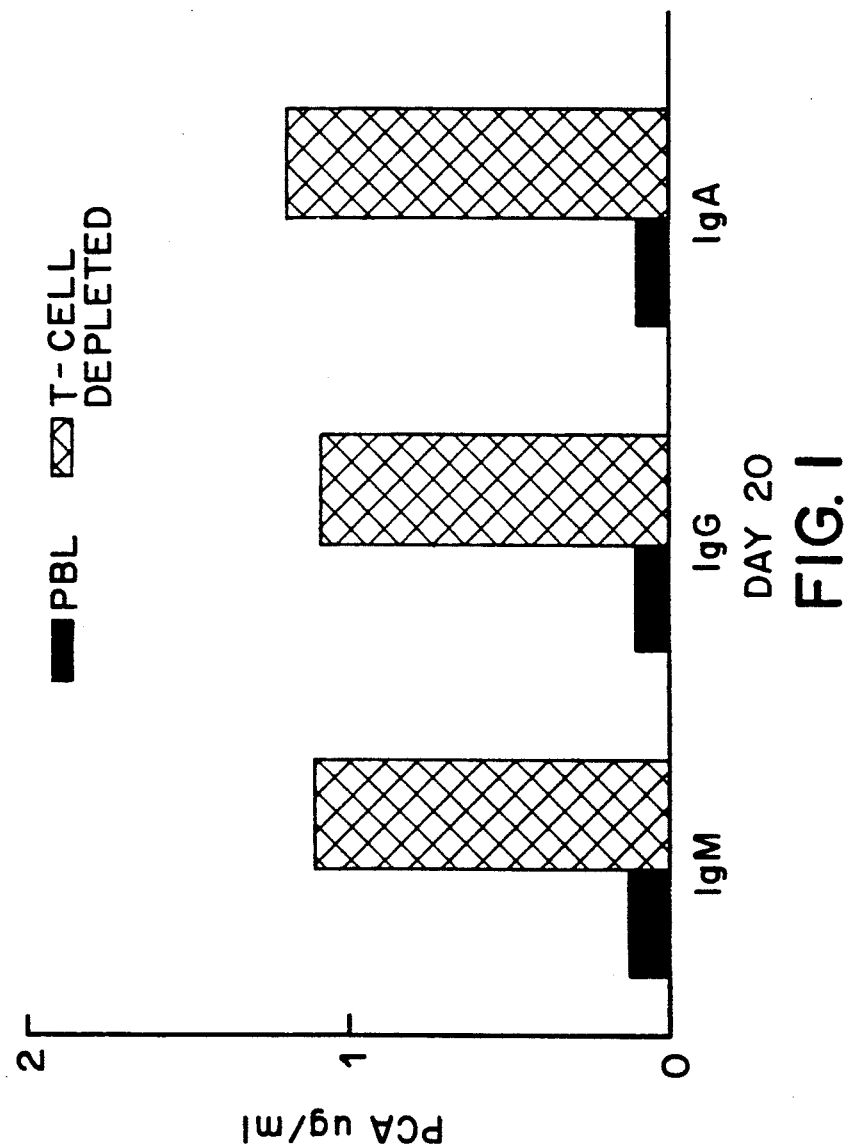
FIG. 1 is a graph showing the effect of T-cells on polyclonal antibody responses in EBV infected peripheral blood lymphocytes.

Human whole blood is collected in heparin containing Vacutainer TM (Becton Dickenson, Rutheford, N.J., USA) tubes. Although this is the preferred method of obtaining whole blood, any other method, such as using a needle and heparin coated syringe, is acceptable. The peripheral blood lymphocytes are separated using a density gradient such as Ficoll-Hypaque TM (Pharmacia Biotechnology Group, Uppsala, Sweden). Other methods that are capable of separating the PBL from the rest of the components of the whole blood are also acceptable.

It has been found that PBL containing T-cells do not produce antigen specific antibodies. Therefore, T-cell depletion of the PBL is the next step. The PBLs are resuspended in physiological buffered saline (PBS), mixed with aminothylisothiouraonium bromide hydrobromide (AET)-sheep red blood cells, placed on ice and then resuspended. Rosetted T-cells are removed by Ficoll-Hypaque density gradient centrifugation, giving T-cell depleted PBL. This rosetting technique is a preferred method, although should other methods prove successful in depleting T-cells from PBL, the resultant PBL may be useful in this invention.

The T-cell depleted PBL are then exposed to transforming agents, resulting in continuously growing cell lines that produce monoclonal antibodies. The preferred method is using EBV as the transforming agent, although any effective lymphotropic virus or other transforming agent able to transform the B-cells to grow in continuous culture and still produce monoclonal antibodies can be used.

The T-cell depleted PBL are then resuspended in EBV infected culture supernatant and incubated for one to two hours at 37 degrees C. After incubation, the EBV infected PBL are plated into the wells of microtiter plates, into which is added in the preferred method, HurIL-4, HurIL-6 (obtained from Genzyme Corporation, Boston, Mass., USA), 8-MG and the antigen. Either of the interleukins may be added alone or in combination with the 8-MG. Sources of IL-4 and IL-6 other than human recombinant may also be used, such as purified human interleukins, murine IL-6 and interleukins found in the supernatants obtained from T-cell lines or from T-cell cultures. The culture medium is a standard medium of Dulbecco's Modified Eagle Medium and Ham's F12 medium (DMEM/F12) (purchased from Gibco, Grand Island, N.Y.) with 10% fetal bovine serum and gentamicin added. The cultures are incubated at 37 deg. C. in a 5% $CO_2$ humidified incubator. Four days later, additional medium is added to each well, and every four days after, supernatant is removed and fresh culture medium is added. Variations to this procedure may be acceptable, as the above is a description of the preferred method.

The supernatant is tested for antigen specific and polyclonal antibody production. The ELISA method has shown that IgG, IgM and IgA immunoglobulin production increases over time in these supernatants, with the IgG immunoglobulin produced in the largest quantities.

These EBV transformed lymphocytes can be cloned using the limiting dilution technique in 96 well microtiter plates with a mouse macrophage cell line as a feeder cell layer. In some cases, irradiated PBL can be used as feeder cells to support the growth of the cloned lymphocytes. Also, these lymphocytes may be fused to an appropriate fusion partner in order to produce a stable, monoclonal producing hybridoma.

The following examples describe the new inventive method. These examples are given merely for illustration of the present invention and are not to be construed as a limitation on the remainder of the specification in any way.

EXAMPLE 1: PREPARATION OF T-CELL DEPLETED PBL a) Human whole blood was collected from donors in heparin containing Vacutainer TM blood collection tubes. The whole blood was diluted in a 1:2 ratio with PBS and layered over Ficoll-Hypaque. The tube containing the Ficoll-Hypaque and the whole blood was centrifuged at 400 g for 20 minutes. The buffy coat layer is removed from the top of the Ficoll-Hypaque and washed three times with PBS.

b) Fresh sheep red blood cells (SRBC) less than two weeks old were washed and centrifuged three times. After the final wash, the packed SRBC were mixed with three volumes of 0.14 M aminothylisothiouraonium bromide hydrobromide (AET) at pH 9.0 for 15 minutes at 37 degrees C. A suspension of AET-SRBC was prepared in PBS.

c) The PBLs were re-suspended in a concentration of $1 \times 10^7$ cells/ml in PBS and mixed with an equal volume of 0.5% AET-SRBC suspension. This mixture was centrifuged at 500 rpm for 5 minutes. The lightly packed cells were placed on ice for 15 minutes. The cells were then gently resuspended and the T-cell depleted PBL were isolated using Ficoll-Hypaque.

EXAMPLE 2: PREPARATION OF THE PBL CULTURE a) Epstein Barr virus containing cell culture supernatants were collected from five to six day old B95 cells (obtained from the American Type Culture Collection in Rockville, Md., USA) and frozen at −70 degrees celsius until needed.

b) The T-cell depleted PBL were resuspended in EBV infected culture supernatant of above at a concentration of $1 \times 10^6$ cells/ml and incubated at 37 degrees C. for one to two hours before plating in 96 well microtiter plates at a final concentration of $2 \times 10^4$ cells/well. HurIL-4 was added to the wells at a final concentration of 100 units/ml, although a range of approximately 5-100 units/ml is acceptable. HurIL-6 was added to each of the wells at a final concentration of 50 units/ml, with a range of approximately 10-100 units/ml being acceptable. 1.0 mM/ml of 8-MG Sigma, St. Louis, Mo., USA), which was dissolved in 0.3 ml of 0.1N NaOH, was added per well. 8-MG can be added in a range of approximately 0.3-1.0 mM/ml. Simultaneously, an antigen was added to each prepared culture well. Ovalbumin, carcinoembryonic antigen (CEA) and HT-29, an irradiated colon cancer cell line, were the antigens used. Twenty-four wells were inoculated with 40 μg of ovalbumin and twenty-four others were inoculated with 400 μg. Forty ng/mL of CEA was used to inoculate each of 54 wells and $2 \times 10^4$ HT-29 cells/well were the inoculum used in another 60 wells. Cultures were incubated at 37 degrees C. in a 5% $CO_2$ humidified incubator for the duration of the experiment. Four days after the initiation of the culture, 50 microliters of culture medium was added to each well. The culture medium consisted of DMEM/F12 with 10% fetal bovine serum and gentamicin added.

Every four days thereafter, 100 microliters of culture supernatants were removed and 100 microliters of fresh culture medium was added per well. The culture supernatants were assayed for polyclonal (PCA) and antigen-specific antibodies.

EXAMPLE 3: ELISA FOR PCA PRODUCTION

The presence of IgG, IgM and IgA antibodies in culture supernatants from Example 2 above was determined by ELISA. Ninety-six well Immulon II (Dynatech, Chantilly, Md.) plates were coated with 0.2 μg/ml goat anti-human IgG or IgA or 0.1 μg/ml goat anti-human IgM (Kirkegaard and Perry Laboratories (KPL), Gaithersburg, Md.). After blocking, 50 microliters of the supernatant was added to each well, and purified human IgG, IgA and IgM, purchased from Cappel Laboratories, Cochranville, Pa., was used as a standard. The plates were incubated for one hour at 37 degress C. Following washing, horseradish peroxidase labeled goat anti-human IgG, IgA, IgM, kappa and lambda light chains, purchased from KPL, were added and then were incubated for one hour at 37 degrees C. After washing, TMB enzyme substrate, supplied by KPL, was added and the plates were incubated at room temperature for 30 minutes. 2N sulfuric acid was added to stop the reaction. The absorbance was read at 450 nm, using a microtiter plate reader. The results are shown in Table 1.

TABLE 1

| | | Polyclonal Antibodies | | |
|---|---|---|---|---|
| | | # positive wells (% +) | | |
| Antigen | # Wells | IgG | IgA | IgM |
| Control-Medium | 24 | 2 (8) | 7 (29) | 15 (62) |
| OVA 400 μg/ml | 32 | 10 (31) | 13 (40) | 23 (72) |
| 40 μg/ml | 32 | 5 (16) | 13 (40) | 22 (69) |
| HT-29 | 60 | 16 (26) | 23 (38) | 54 (90) |
| CEA | 54 | 29 (53) | 13 (24) | 45 (83) |

The isotype specific polyclonal antibody response was increased in wells receiving 8-MG and IL-4 and IL-6 in the presence of antigen when compared to control cultures containing medium alone. The percentage increase of the IgG and IgA isotypes was greater than that of the IgM, in most cases.

Antigen-specific ELISA were performed similarly as above with the antigen of interest coated on the plate at the following concentrations: OVA, 10 μg/ml and CEA, 3.0 μg/ml. The results are shown in Table 2.

TABLE 2

| | | Antigen-Specific Antibody | |
|---|---|---|---|
| | | # Positive Wells (% +) | |
| Antigen | # Wells | Primary Screen # Wells (%) | 3rd Passage # Wells (%) |
| OVA 400 μg/ml | 32 | 19 (59) | 19 (59) |
| 40 μg/ml | 32 | 11 (21) | 9 (28) |
| HT-29* | 60 | 9 (15) | 7 (12) |
| CCA 40 ng/ml | 54 | 21 (39) | 14 (26) |

*Assayed for CEA

Supernatants obtained from wells containing medium alone showed no antigen specific response to OVA or CEA when screened in the primary assay. While culture supernatants obtained from antigen stimulated wells showed a high number of antigen specific wells as compared to the control and also that the production of antigen specific antibodies continued through the third passage of cells, a time span of approximately 11 weeks.

Figure 2:
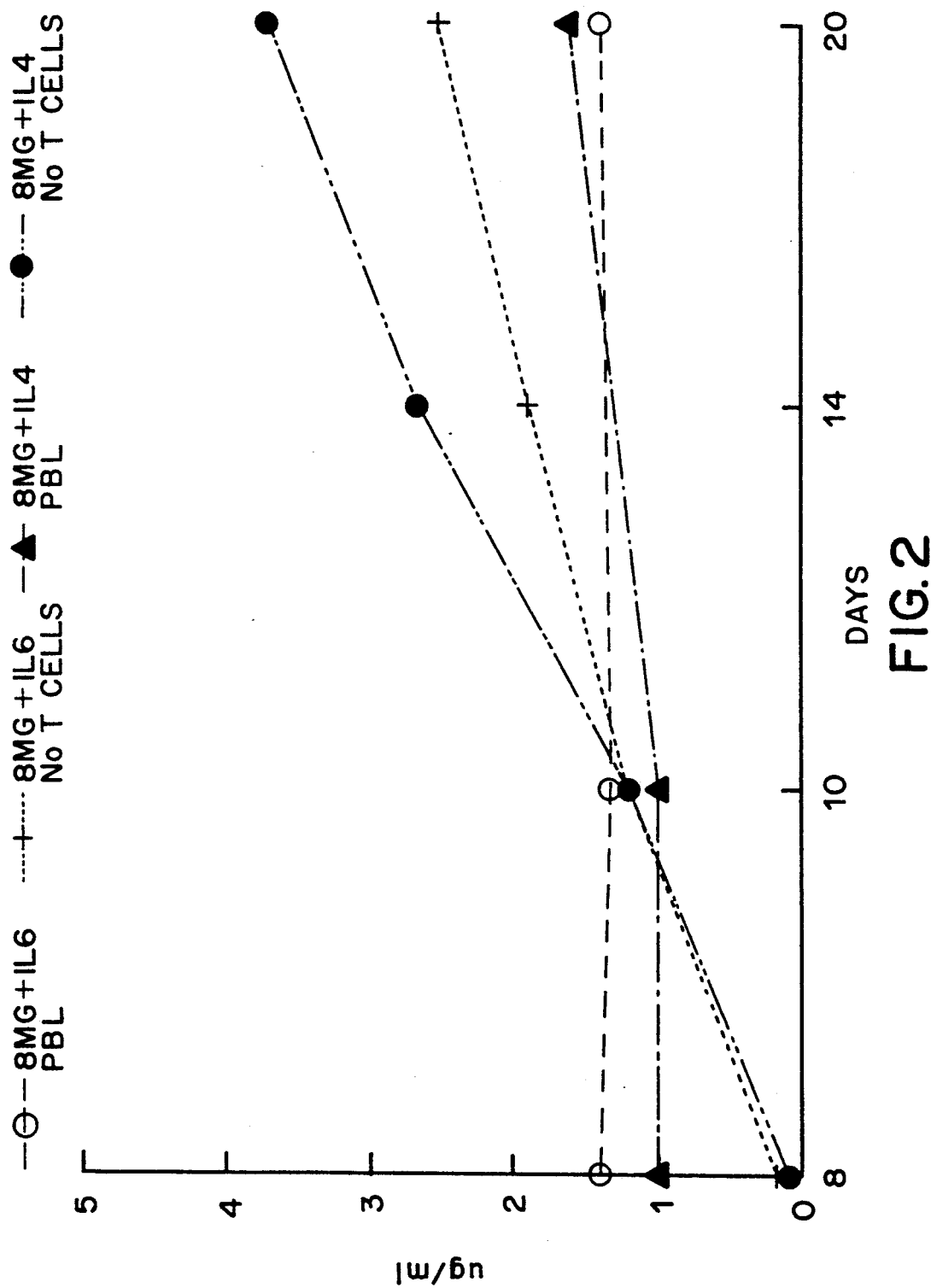
FIG. 2 is a graph showing the polyclonal antibody response of EBV treated B-cells, in particular, the effect of T-cells on IgG production.
Figure 3:
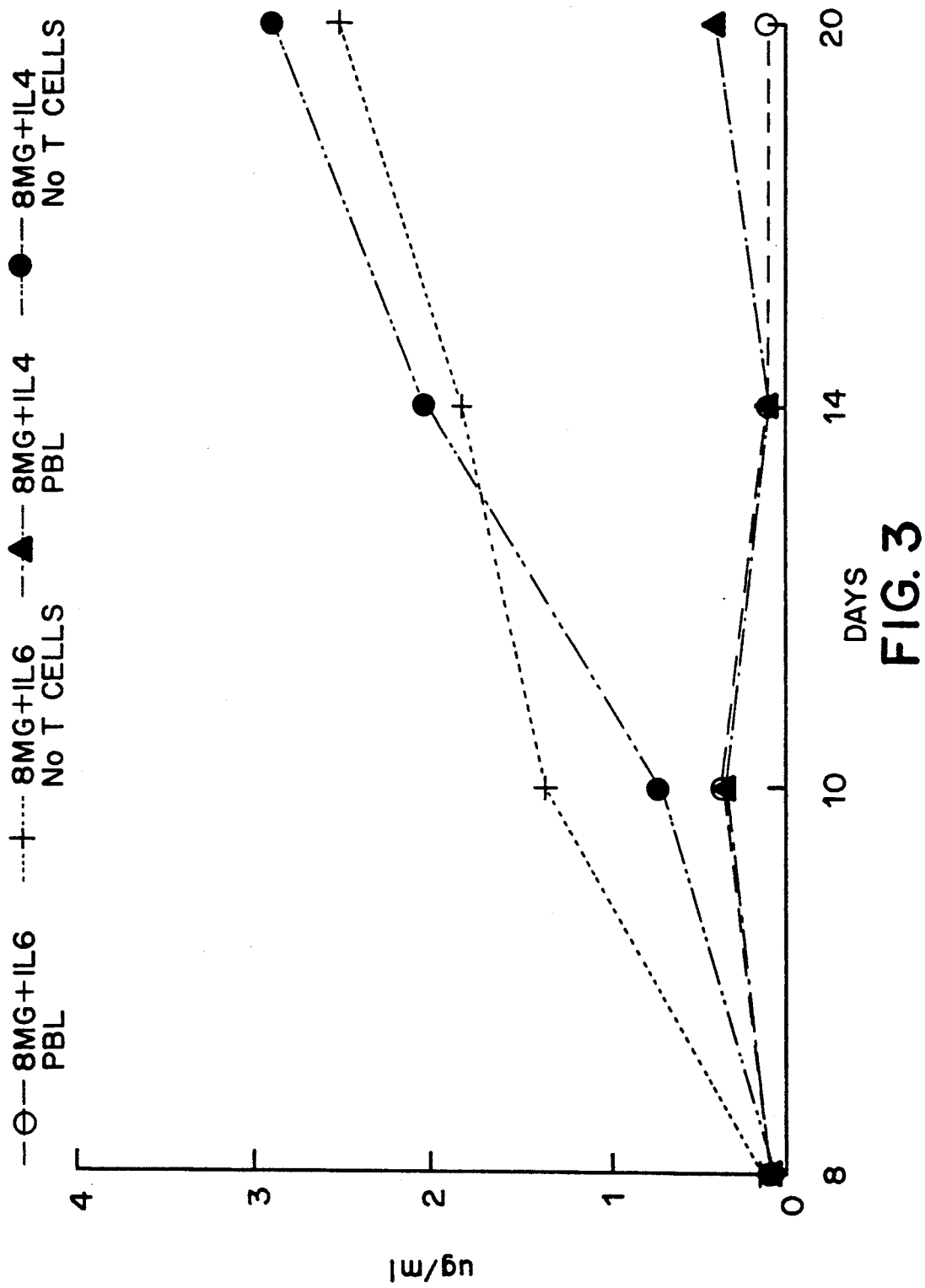
FIG. 3 is a graph similar to FIG. 2, showing instead the effects of T-cells on IgA production.
Figure 4:
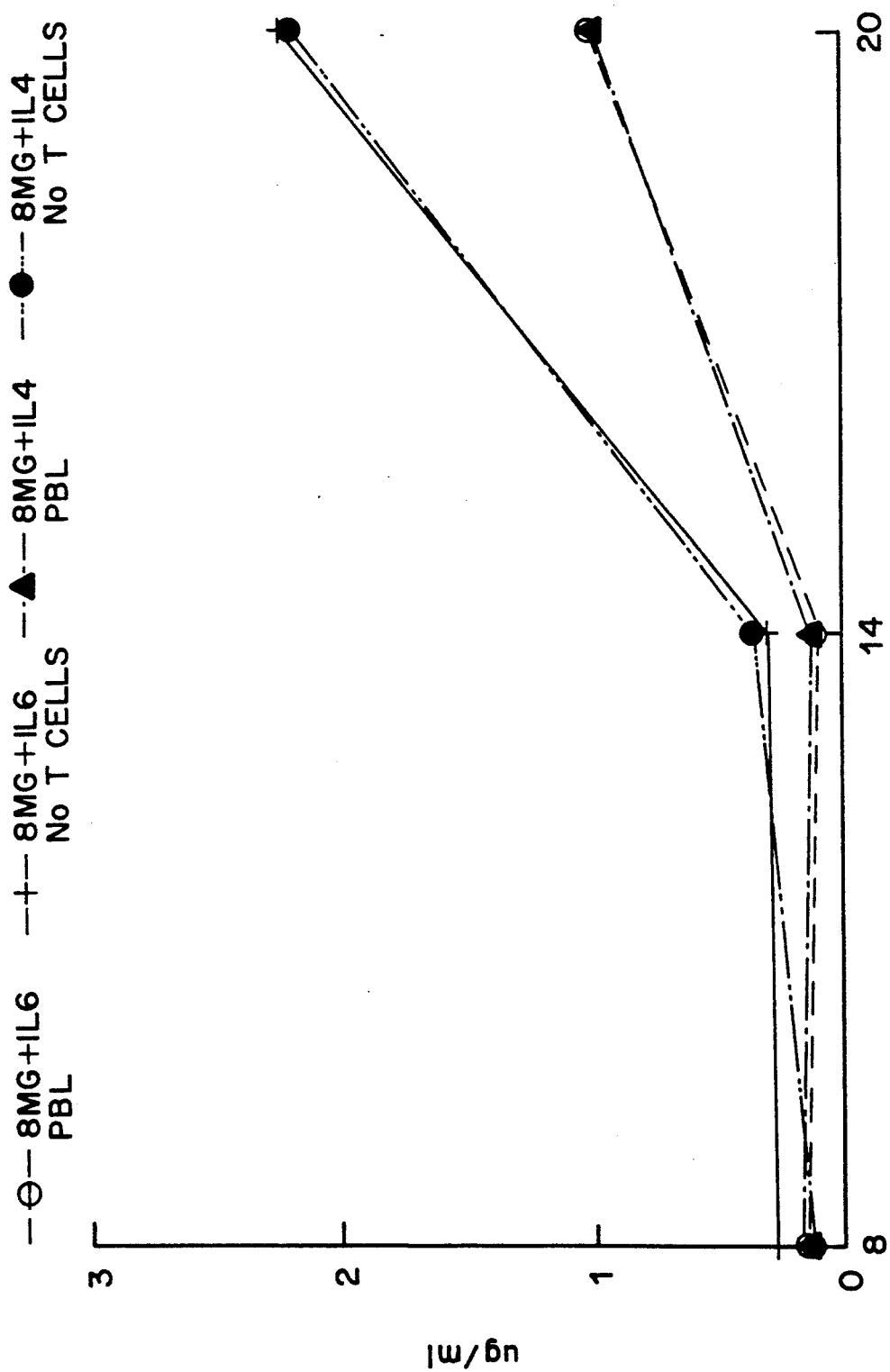
FIG. 4 is a graph similar to FIG. 2, showing instead the effects of T-cells on IgM production.

EXAMPLE 4: COMPARISON OF T-CELL DEPLETED AND NONDEPLETED SYSTEMS a) In order to determine the effect of T-cell depletion on the inventive method, systems using depleted and non-depleted PBL were used. PBL were collected from donors and separated as described in Example 1. Half of the cells were treated with AET-SRBC as described in Example 1 and half were not. The experiment was conducted as described in Example 2 except that heterologous human RBC's were the only antigen used, in concentrations of $2 \times 10^3$ and $5 \times 10^2$, and 96 wells were used for each type of PBL preparation. FIG. 1 shows that the T-cell depleted PBL wells used as controls that contained medium alone produced approximately 10-fold more immunoglobulin of each of the isotypes tested.

b) FIGS. 2, 3 and 4 represent a summary of data comparing the effects of 8-MG plus IL-6 and 8MG plus IL-4 over time in the cultures described in a) above. IgM, IgG and IgA immunoglobulin production increased over time in supernatants from the T cell depleted cultures, with IgG being produced in the highest quantities. The combination of IL-6 and 8-MG enhanced the production of IgG as compared to 8-MG and IL-4.

Cultures receiving nondepleted PBL did produce up to 1 μg/ml of IgM PCA, while little or no increase in IgA and IgG was observed.

Table A shows the micrograms/ml of IgG, IgA and IgM present at day 20 in both T-cell depleted and non-depleted culture systems.

TABLE A

| Culture | Day 20 μg/ml of Antibody. (fold increase) | | |
| --- | --- | --- | --- |
| | IgM | IgG | IgA |
| Medium-Whole PBL | 0.126 | 0.1 | 0.1 |
| Medium-T-Cell Depleted | 1.11 (8.8) | 1.08 (10.8) | 1.19 (11.9) |
| 8-MG + IL-4 T-Cell Depleted | 2.18 (17) | 3.72 (37.2) | 2.87 (28.7) |
| 8-MG + IL-6 T-Cell Depleted | 2.22 (17.6) | 2.53 (25.3) | 2.5 (25.0) |

Figure 5:
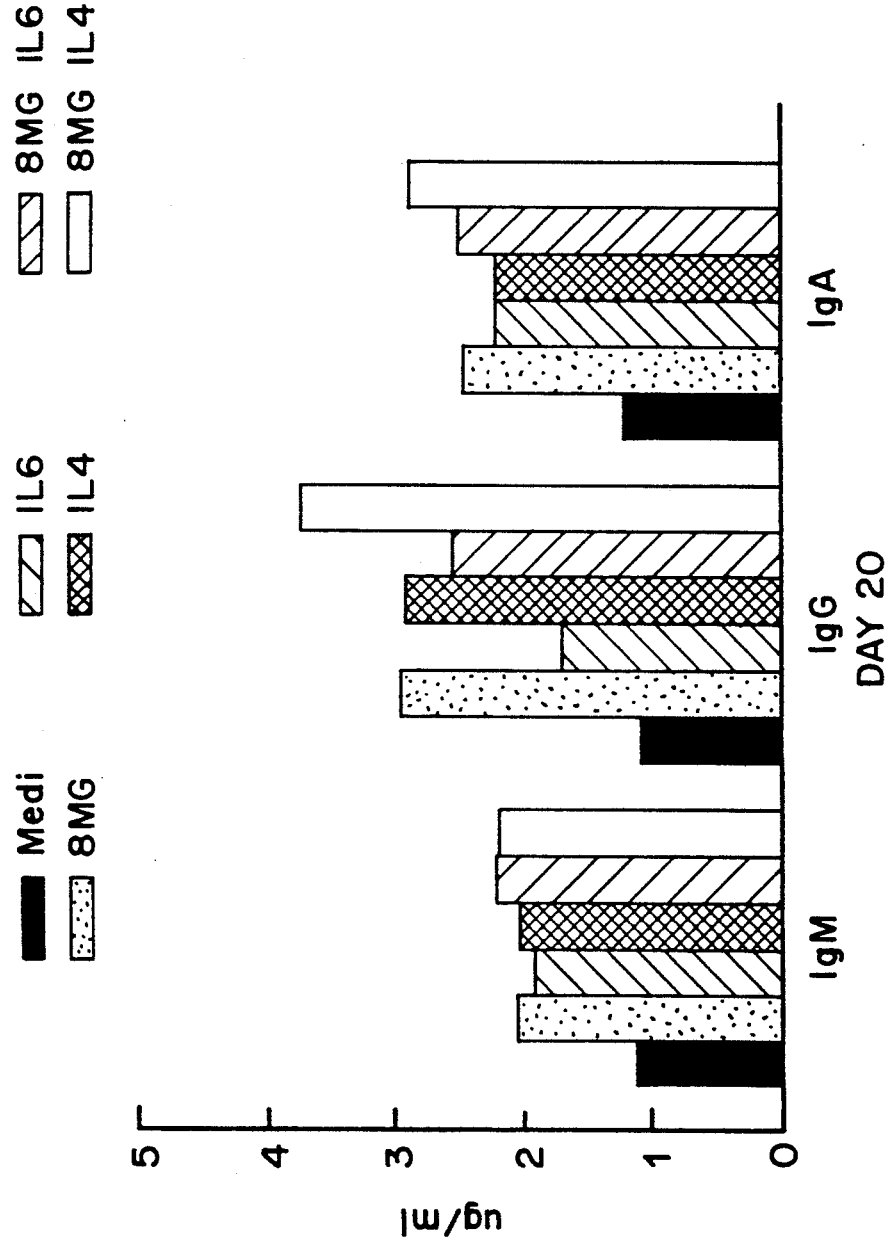
FIG. 5 is a graph showing the polyclonal antibody response of EBV infected peripheral blood lymphocytes to which various reagents have been added.

This table shows an increase of 20–40 fold of the immunoglobulins produced in supernatants from cultures containing T-cell depleted PBL and the adjuvants 8-MG and IL-4, and 8-MG and IL-6, over the non-depleted PBL cultures without adjuvants.

c) FIG. 5 represents data demonstrating that 8-MG, IL-4 and IL-6 each enhance the polyclonal antibody response of T-cell depleted PBL when compared to cells incubated in medium alone. The combination of 8-MG and IL-4 resulted in an increase in IgG over that observed with each reagent alone.

EXAMPLE 5: ANTIGEN-SPECIFIC ANTIBODY PRODUCTION

Heterologous human RBC's, in a concentration of $4 \times 10^3$ RBC/well, were used as the sole antigen in an experiment performed as in Example 2. Results suggest that 8-MG may play a role in directing antigen-specific responsiveness in vitro.

Hemagglutination assays (HA) were performed to measure the presence of anti-RBC antibodies. The final culture supernatants were mixed with 1% RBC (25 microliter each) in a HA plate and incubated at room temperature for one hour. The plates were tipped at a forty-five degree angle and examined for agglutination. Wells that demonstrated direct HA activity were noted and the plates washed three times in PBS. Goat anti-human Ig (1:100) was added to each well, mixed and left at room temperature for one hour. The plates were tipped at a forty-five degree angle and examined for agglutination. The results are shown in Table 3.

TABLE 3

| Development of Antigen-Specific Antibodies in vitro Toward Heterologous RBC | |
| --- | --- |
| Groups* | # of HA positive Wells |
| RBC | 1 |
| RBC + IL-4 (10 u/ml) | 0 |

TABLE 3-continued

| Development of Antigen-Specific Antibodies in vitro Toward Heterologous RBC | |
| --- | --- |
| Groups* | # of HA positive Wells |
| RBC + 8 MG (0.1 mM) | 1 |
| RBC + 8 MG (0.3 mM) | 1 |
| RBC + 8 MG (1.0 mM) | 7 |

*16 wells/group

Nine of the 10 positive wells also received 8-MG at the initiation of the culture period. Seven wells receiving the highest dose of 8MG tested, 1 mM, were HA positive, strongly suggesting an important contribution of this reagent in enhancing antigen-specific antibody development in vitro. The addition of IL-4 and/or IL-6 to the cultures enhanced the PCA response over that observed with 8-MG alone (seen in FIG. 5) but did not appear to increase the incidence of antigen-specific antibodies over that observed with 8-MG alone when RBC were used as the antigen.

EXAMPLE 6: MOLT-3 HIV LYSATE AS ANTIGEN

In one experiment Molt-3 HIV lysate was added to the cultures. Of the wells receiving 8-MG and viral lysate, 5 of 64 wells produced antibodies that reacted in ELISA with Molt-3 and Molt-3HIV lysate. When IL-6 was added to the same combination in vitro, supernatants from 8 of 16 wells contained antibodies specific to the immunizing agent. In this antigenic system the addition of the lymphokine did appear to enhance the immunomodulatory activity of 8-MG.

EXAMPLE 7: CLONING OF HUMAN PBL

EBV transformed, antigen specific PBL as described in Example 2 are cloned using a limiting dilution technique known to those skilled in the art. J774 mouse macrophage cell line (American Type Culture Collection Number ATCC TIB67, J774 A.1, Rockville, Md., USA) is used as a feeder cell layer. Irradiated PBL can also be used as the feeder cells in some cases.

I claim:

1. A method for amplifying production of antigen specific human IgG and IgA monoclonal antibodies comprising
   a) obtaining human peripheral blood lymphocytes (PBL),
   b) depleting T-cells from said PBL,
   c) transforming the T-cell depleted PBL with a transforming agent in the presence of antigen and the adjuvants 8-mercaptoguanosine and at least one selected from the group consisting of IL-4 and IL-6,
   d) identifying cells producing antigen specific IgG and IgA antibodies, and
   e) cloning said identified cells.

2. A method according to claim 1, wherein the adjuvants are 8-mercaptoguanosine, IL-4 and IL-6.

3. A method according to claim 1, wherein the transforming agent is Epstein Barr virus.

4. A method for amplifying production of antigen specific human IgM monoclonal antibodies comprising
   a) obtaining human peripheral blood lymphocytes,
   b) depleting T-cells from said PBL,
   c) transforming the T-cell depleted PBL with a transforming agent in the presence of antigen and the adjuvants 8-mercaptoguanosine and at least one selected from the group consisting of IL-4 and IL-6, d) identifying cells producing antigen specific IgM antibodies, and e) cloning said identified cells.

5. A method according to claim 4, wherein the adjuvants are 8-mercaptoguanosine, IL-4 and IL-6.

6. A method according to claim 4, wherein the transforming agent is Epstein Barr virus.

7. A method for amplifying production of human immunoglobulins comprising a) obtaining human peripheral blood lymphocytes, b) depleting T-cells from said PBL, c) transforming the T-cell depleted PBL with a transforming agent in the presence of 8-mercaptoguanosine at least one of the adjuvants selected from the group consisting of IL-6 and IL-4, and d) culturing the transformed PBL in the presence of 8-mercaptoguanosine and at least one of IL-4 or IL-6, thereby producing immunoglobulins.

8. A method according to claim 7, wherein the transforming agent is Epstein Barr virus.

* * * * *